(12) United States Patent
Abdelwahed et al.

(10) Patent No.: US 10,974,034 B2
(45) Date of Patent: Apr. 13, 2021

(54) FORCE MEASUREMENT INSTRUMENT FOR SINUPLASTY PROCEDURE

(71) Applicants: Acclarent, Inc., Irvine, CA (US); Biosense Webster (Israel) Ltd., Yokneam (IL)

(72) Inventors: Hany Abdelwahed, Irvine, CA (US); Babak Ebrahimi, Irvine, CA (US); Ehsan Shameli, Irvine, CA (US); Assaf Govari, Haifa (IL); Andres Claudio Altmann, Haifa (IL); Vadim Gliner, Haifa (IL); Yehuda Algawi, Binyamina (IL)

(73) Assignees: Acclarent, Inc., Irvine, CA (US); Biosense Webster (Israel) Ltd., Yokneam (IL)

(*) Notice: Subject to any disclaimer, the term of this patent is extended or adjusted under 35 U.S.C. 154(b) by 109 days.

(21) Appl. No.: 16/212,851

(22) Filed: Dec. 7, 2018

(65) Prior Publication Data
US 2019/0175888 A1 Jun. 13, 2019

Related U.S. Application Data

(63) Continuation-in-part of application No. 15/837,749, filed on Dec. 11, 2017.

(51) Int. Cl.
*A61M 29/02* (2006.01)
*A61M 25/06* (2006.01)
(Continued)

(52) U.S. Cl.
CPC ........... *A61M 29/02* (2013.01); *A61B 5/6843* (2013.01); *A61B 5/6851* (2013.01);
(Continued)

(58) Field of Classification Search
CPC ...... A61M 29/00; A61M 25/10; A61M 25/00; A61B 17/24; A61B 17/12104; A61B 1/233; A61F 5/08
See application file for complete search history.

(56) References Cited

U.S. PATENT DOCUMENTS 5,030,227 A * 7/1991 Rosenbluth ........ A61M 25/1011
600/116
9,155,492 B2 10/2015 Jenkins et al.
(Continued)

FOREIGN PATENT DOCUMENTS

JP 2007-222666 A 9/2007
JP 2008-264119 A 11/2008
(Continued)

OTHER PUBLICATIONS

International Search Report and Written opinion dated Mar. 26, 2019 for Application No. PCT/IB2018/059870, 14 pages.

*Primary Examiner* — Darwin P Erezo
*Assistant Examiner* — Brigid K Byrd
(74) *Attorney, Agent, or Firm* — Frost Brown Todd LLC

(57) ABSTRACT

A dilation instrument includes a body, a dilation catheter, a guide member, and a force sensor. The dilation catheter has an expandable dilator. The guide member extends distally from the body and is configured to guide movement of the expandable dilator. The force sensor is operatively connected to the guide member and is configured to sense a force imparted against the guide member for monitoring engagement with an anatomy of a patient.

20 Claims, 11 Drawing Sheets

(51) Int. Cl.
*A61M 25/09* (2006.01)
*A61M 3/02* (2006.01)
*A61B 5/00* (2006.01)
*A61B 90/00* (2016.01)
*A61M 25/00* (2006.01)
*A61M 25/01* (2006.01)

(52) U.S. Cl.
CPC ............ *A61B 5/6852* (2013.01); *A61B 90/06* (2016.02); *A61M 3/0295* (2013.01); *A61M 25/0662* (2013.01); *A61M 25/09* (2013.01); *A61M 25/09041* (2013.01); *A61B 2090/064* (2016.02); *A61B 2090/065* (2016.02); *A61B 2562/0261* (2013.01); *A61M 25/0041* (2013.01); *A61M 25/0113* (2013.01); *A61M 2025/09116* (2013.01); *A61M 2205/18* (2013.01); *A61M 2205/332* (2013.01); *A61M 2205/3327* (2013.01); *A61M 2205/50* (2013.01); *A61M 2205/581* (2013.01); *A61M 2205/582* (2013.01); *A61M 2210/0675* (2013.01); *A61M 2210/0681* (2013.01)

(56) References Cited

U.S. PATENT DOCUMENTS

| | | | |
|---|---|---|---|
| 9,962,530 B2 | 5/2018 | Johnson et al. | |
| 10,137,285 B2 | 11/2018 | Jenkins et al. | |
| 10,137,286 B2 | 11/2018 | Lin et al. | |
| 2006/0004323 A1* | 1/2006 | Chang | A61F 2/82 604/28 |
| 2007/0151391 A1 | 7/2007 | Larkin et al. | |
| 2007/0208252 A1* | 9/2007 | Makower | A61B 6/037 600/424 |
| 2008/0183128 A1 | 7/2008 | Morriss et al. | |
| 2008/0245371 A1* | 10/2008 | Gruber | A61B 17/22 128/831 |
| 2010/0022950 A1* | 1/2010 | Anderson | A61B 18/1492 604/100.01 |
| 2010/0030031 A1 | 2/2010 | Goldfarb et al. | |
| 2010/0049062 A1 | 2/2010 | Ziv | |
| 2011/0004057 A1 | 1/2011 | Goldfarb et al. | |
| 2011/0015483 A1 | 1/2011 | Barbagli et al. | |
| 2011/0263934 A1 | 10/2011 | Aeby et al. | |
| 2012/0071857 A1 | 3/2012 | Goldfarb et al. | |
| 2013/0158477 A1 | 6/2013 | Goldenberg et al. | |
| 2014/0074141 A1 | 3/2014 | Johnson et al. | |
| 2014/0277060 A1* | 9/2014 | Ranade | A61M 25/10184 606/192 |
| 2014/0309550 A1* | 10/2014 | Iglesias | A61B 5/205 600/561 |
| 2015/0223707 A1 | 8/2015 | Ludoph | |
| 2016/0310714 A1 | 10/2016 | Jenkins et al. | |
| 2017/0120020 A1 | 5/2017 | Lin et al. | |
| 2019/0175886 A1 | 6/2019 | Abdelwahed et al. | |

FOREIGN PATENT DOCUMENTS

| | | |
|---|---|---|
| WO | WO 1999/045994 A1 | 9/1999 |
| WO | WO 2007/098494 A1 | 8/2007 |
| WO | WO 2016/172696 A1 | 10/2016 |
| WO | WO 2018/080769 A1 | 5/2018 |

* cited by examiner

FORCE MEASUREMENT INSTRUMENT FOR SINUPLASTY PROCEDURE

PRIORITY

This application is a continuation-in-part of U.S. patent application Ser. No. 15/837,749, entitled "Force Measurement Instrument for Sinuplasty Procedure," filed Dec. 11, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

While an endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MIl scan, 3-D map, etc.) so as to superimpose the current location of the instrument on the preoperatively obtained images. In some IGS procedures, a digital tomographic scan (e.g., CT or MIl, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Irvine, Calif.; systems available from Surgical Navigation Technologies, F Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
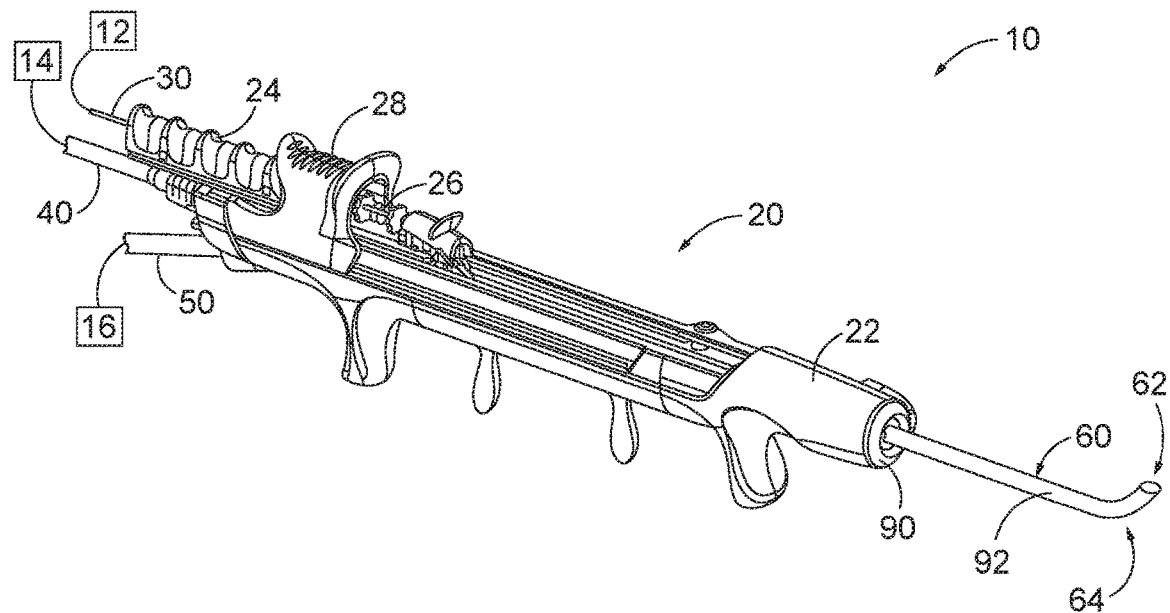
FIG. 1A depicts a perspective view of an exemplary dilation instrument assembly, with an exemplary guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "upper" and "lower" also are used herein with respect to directions transverse to "proximal and "distal" directions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D shows a first exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) is part of an IGS system as described below with respect to FIGS. 2-3. In some other versions, guidewire power source (12) comprises a source of light as described below with respect to FIGS. 4-6. In the present example shown in FIGS. 1A-1D, inflation source (14) comprises a source of saline. However, it should be understood that any other suitable source of fluid (liquid or otherwise) may be used. Also in the present example, irrigation fluid source (16) comprises a source of saline. Again, though, any other suitable source of fluid may be used. It should also be understood that flush fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22). It should therefore be understood that dilation instrument (20) may be fully operated by a single hand of a human operator.

A. Exemplary Guide Catheter

A guide catheter (60) extends distally from handle body (22). Guide catheter (60) includes an open distal end (62) and a bend (64) formed proximal to open distal end (62). In the present example, dilation instrument (20) is configured to removably receive several different kinds of guide catheters (60), each guide catheter (60) having a different angle formed by bend (64). These different angles may facilitate access to different anatomical structures. Various examples of angles and associated anatomical structures are described in one or more of the references cited herein; while further examples will be apparent to those of ordinary skill in the art in view of the teachings herein. Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60), relative to handle body (22), about the longitudinal axis of the straight proximal portion of guide catheter (60), thereby further promoting access to various anatomical structures.

Guide catheter (60) is removable from handle body (22) for replacement with an unused guide catheter (60) or an alternative guide catheter having a different bend for accessing different anatomical structures. Guide catheter (60) further includes a hub (90) having a guide tube (92) extending distally therefrom. Hub (90) is received within a port (94) (see FIG. 2) and configured to removably connect therein for securing guide tube (92) relative to handle body (22). In the present example, dilation instrument assembly (10) further includes an exemplary force measurement system (100) (see FIG. 2) at the interface of at least one of hub (90), port (94) (see FIG. 2), and guide tube (92). Force measurement system (100) (see FIG. 2) is configured to monitor force applied to guide tube (92) in use as discussed below in greater detail.

B. Exemplary Guidewire

Dilation instrument (30) further comprises an exemplary guidewire (30), which is coaxially disposed in guide catheter (60). Guidewire slider (24) is secured to guidewire (30) such that translation of guidewire slider (24) relative to handle body (22) provides corresponding translation of guidewire (30) relative to handle body (22). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, guidewire (30) includes a preformed bend formed just proximal to a distal end (32) of guidewire (30). In such versions, the preformed bend and the rotatability provided via guidewire spinner (26) may facilitate alignment and insertion of distal end (32) into a sinus ostium, Eustachian tube, or other passageway to be dilated. Also in some versions, guidewire (30) includes at least one optical fiber extending to a lens or other optically transmissive feature in distal end (32), such as illuminating guidewire (150) (see FIGS. 4-6) discussed below. Optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure.

By way of example only, guidewire (30) may be configured in accordance with at least some of the teachings of U.S. Pat. No. 9,155,492, the disclosure of which is incorporated by reference herein. In some versions, guidewire (30) is configured similar to the Relieva Luma Sentry™ Sinus Illumination System by Acclarent, Inc. of Irvine, Calif. In addition to, or as an alternative to, including one or more optical fibers, guidewire (30) may include a sensor and at least one wire that enables guidewire (30) to provide compatibility with an IGS system as described in greater detail below. Other features and operabilities that may be incorporated into guidewire (30) will be apparent to those of ordinary skill in the art in view of the teachings herein.

C. Exemplary Dilation Catheter

Dilation instrument (30) further comprises a dilation catheter (40), which is coaxially disposed in guide catheter (60). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (62) of guide catheter (60). As can also be seen in FIG. 1C, a distal portion of guidewire (30) protrudes distally from the open distal end of dilation catheter (40) when guidewire (30) and dilation catheter are both in distal positions.

Dilation catheter (40) of the present example comprises a non-extensible balloon (44) located just proximal to an open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pat. No. 9,962,530, entitled "Inflator for Dilation of Anatomical Passageway," issued May 8, 2018, the disclosure of which is incorporated by reference herein. Other suitable configurations that may be used to provide a source of pressurized fluid will be apparent to those of ordinary skill in the art in view of the teachings herein.

While not shown, it should be understood that dilation catheter (40) may include at least two separate lumens that are in fluid isolation relative to each other. One lumen may provide a path for fluid communication between balloon (44) and inflation source (14). The other lumen may provide a path to slidably receive guidewire (30).

While dilation catheter (40) of the present example is configured to transition between a non-dilated state and a dilated state based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra™ Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pat. No. 7,630,676, entitled "Methods, Devices and Systems for Treatment and/or Diagnosis of Disorders of the Ear, Nose and Throat," issued Dec. 8, 2009, the disclosure of which is incorporated by reference herein. Of course, irrigation may be provided in the absence of a dilation procedure; and a dilation procedure may be completed without also including irrigation. It should therefore be understood that dilation fluid source (16) and tube (50) are merely optional.

E. Exemplary Variations

In the present example, guidewire (30) is coaxially disposed within dilation catheter (40), which is coaxially disposed within guide catheter (60). In some other versions, guide catheter (60) is omitted from dilation instrument (20). In some such versions, a malleable guide member is used to guide guidewire (30) and dilation catheter (40). In some such versions, guidewire (30) is omitted and dilation catheter (40) is slidably disposed about the exterior of the internal malleable guide member. In some other versions, guidewire (30) is slidably disposed about the exterior of the internal malleable guide member; and dilation catheter (40) is slidably disposed about the exterior of guidewire (30). In still other versions, guidewire (30) is slidably disposed within the interior of the malleable guide member; and dilation catheter (40) is slidably disposed about the exterior of the malleable guide member.

By way of example only, versions of dilation instrument (20) that include a malleable guide member may be constructed and operable in accordance with at least some of the teachings of U.S. Pat. No. 10,137,285, entitled "Balloon Dilation System with Malleable Internal Guide," issued Nov. 27, 2018, the disclosure of which is incorporated by reference herein. As another merely illustrative example, versions of dilation instrument (20) that include a malleable guide member may be constructed and operable in accordance with at least some of the teachings of U.S. Pat. No. 10,137,286, entitled "Apparatus for Bending Malleable Guide of Surgical Instrument," issued Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

It should be understood that the variations of dilation instrument (20) described below in the context of an IGS system may be incorporated into versions of dilation instrument (20) having a malleable guide just like the variations of dilation instrument (20) described below in the context of an IGS system may be incorporated into versions of dilation instrument (20) having a rigid guide catheter (60).

Various examples below describe the use of an IGS system to provide navigation of instruments within a patient. In particular, various examples below describe how dilation instrument assembly (10) may be modified to incorporate IGS system features. However, it should also be understood that dilation instrument assembly (10) may be used in conjunction with conventional image guidance instruments, in addition to being used with IGS system components. For instance, dilation instrument assembly (10) may be used in conjunction with an endoscope, at least to provide initial positioning of guide catheter (60) in a patient. By way of example only, such an endoscope may be configured in accordance with at least some of the teachings of U.S. Pub. No. 2010/0030031, now abandoned, the disclosure of which is incorporated by reference herein. Other suitable kinds of endoscopes that may be used with the various versions of dilation instrument assembly (10) described herein will be apparent to those of ordinary skill in the art.

II. Exemplary Force Measurement System

Figure 2:
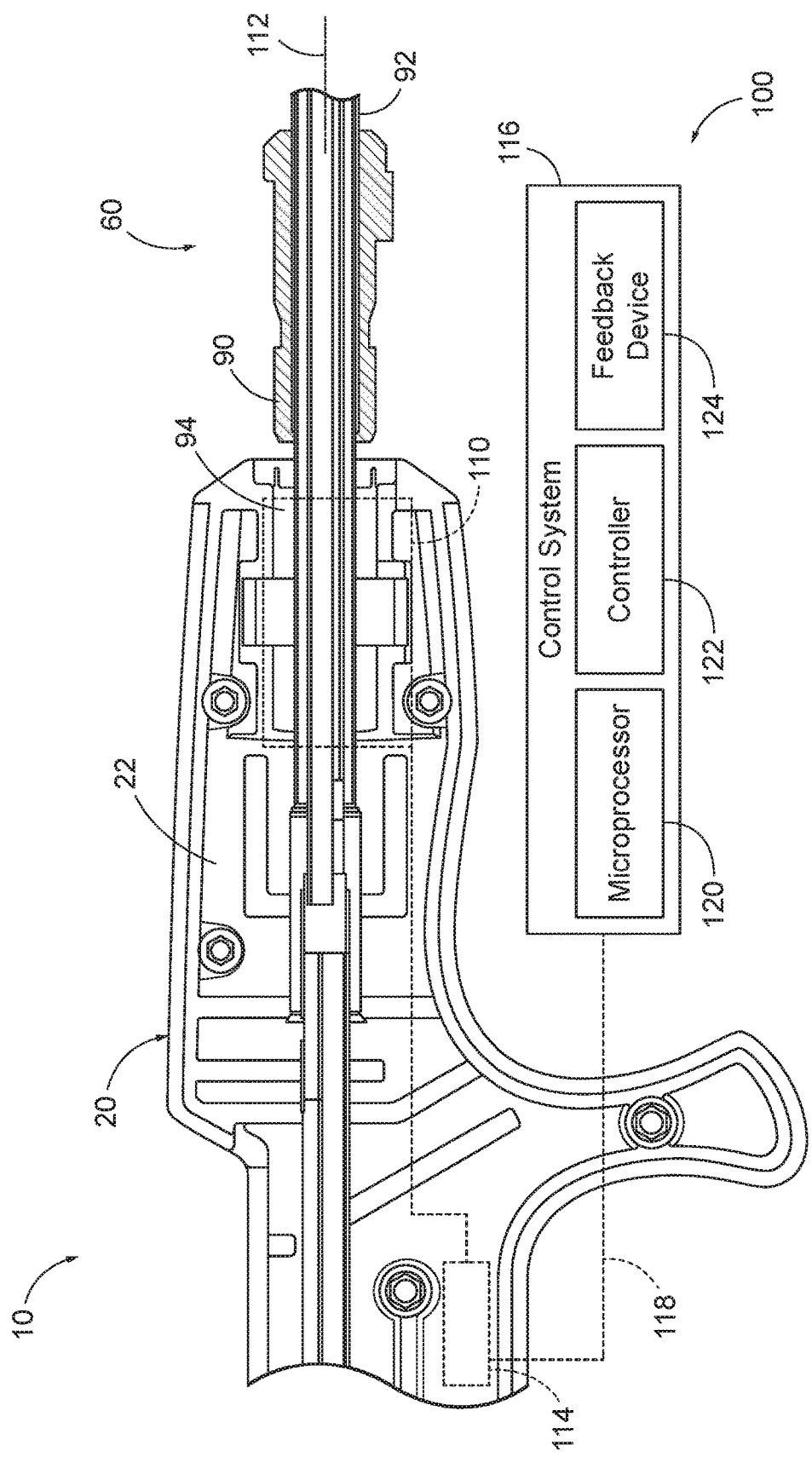
FIG. 2 depicts an enlarged sectional view of the dilation instrument assembly of FIG. 1A taken along a centerline thereof and having various features of a force measurement system schematically illustrated therein.

FIG. 2 shows exemplary force measurement system (100) discussed briefly above and incorporated into dilation instrument (20). In some instances, force measurement system (100) is used during a procedure for dilating an anatomical passageway, such as the ostium of a paranasal sinus or other passageway within the ear, nose, or throat. However, it should be understood that force measurement system (100) may be readily used in various other kinds of procedures. To this end, force measurement system (100) of the present example is configured to measure force applied to a guide catheter having a guide tube, such as exemplary guide tubes (92, 192, 292, 392) shown in FIGS. 1A, 6, 12 and 13. The measured force may then be monitored to provide the clinician with information for inhibiting overloading dilation instrument (20) and/or the anatomy along the anatomical passageway. In some examples, such overloading may damage dilation instrument (20) and/or the anatomy. For instance, in procedures where dilation instrument (20) is used in a head of a patient, distal end (62) of guide catheter (60) may approach regions where distal end (62) may present a risk of damaging the patient's optic nerve or brain if distal end (62) is urged against an anatomical structure with too much force. Thus, monitoring the force applied to guide tube (92, 192, 292, 392) may provide the clinician with notice to actively adjust manipulation of dilation instrument (20) to improve patient outcomes.

A schematic representation of a multi-directional sensor assembly (110) is shown in FIG. 2 positioned within port (94) of handle body (22) to engage with and operatively connect to hub (90) of guide catheter (60). Guide tube (92) extends distally from hub (90) and defines a longitudinal axis (112) within a proximal end portion thereof. Guide tube (92) is rigidly secured within hub (90) such that force applied to guide tube (92) during use transfers through hub (90) and to multi-directional sensor assembly (110) for detection. In the present example, multi-directional sensor assembly (110) is configured to detect the force applied to guide tube (92) along three distinct component directions including a longitudinal force component, a transverse force component, and a torque component. The longitudinal force component extends in the axial direction of the longitudinal axis, the transverse force component extends in a transverse direction to the longitudinal axis, and the torque component is a moment of the force in a rotational direction about the longitudinal axis. While multi-directional sensor assembly (110) is configured to simultaneously detect the longitudinal force, transverse force, and torque components, it will be appreciated that additional, distinct force components may be detected in alternative examples or that less force components may be detected in still other alternative examples. The invention is thus not intended to be unnecessarily limited to simultaneous measurement or lone measurement of longitudinal force, transverse force, and torque components.

Force measurement system (100) further includes a data acquisition module (114) and a control system (116) for collecting data regarding detected force on guide tube (92), measuring the values of the detected force, and monitoring the force values during use, and controlling system response. Data acquisition module (114) is shown schematically contained within handle body (22) and operatively connected to multi-directional sensor assembly (110). In contrast, control system (116) is shown schematically shown external of handle body (22) and connected to data acquisition module (114) via a data transfer wire (118). In an alternative example, the entire force measurement system (100) may be supported on handle body (22). In still another example, other portions of force measurement system (100) may be wired to handle body (22) wirelessly connected to handle body (22). The invention is thus not intended to be unnecessarily limited to the particular arrangement of force measurement system (100) integrated into handle body (22).

Data acquisition module (114) receives the detected force from multi-directional sensor assembly (110) in the longitudinal force, transverse force, and torque components and converts the detected force components to measured force component values. Data acquisition module (114) may include an application specific integrated circuit (ASIC), a microprocessor, a memory chip or other memory device, and/or other components. Various components and configurations that may be incorporated into data acquisition module (114) will be apparent to those skilled in the art in view of the teachings herein. In some variations, data acquisition module (114) is effectively integrated into control system (116). It is therefore not required to have a separate data acquisition module (114) and control system (116) as shown in FIG. 2.

In the present example, the measured force component values are communicated via data transfer wire from data acquisition module (112) to control system (116), which includes a microprocessor (120), a controller (122), and a feedback device (124). Microprocessor (120) processes the measured force component values in real-time for storage in a memory (not shown) and/or and monitoring, such as comparison to one or more predetermined threshold values. In the present example, the predetermined threshold values include a predetermined maximum longitudinal force, a predetermined maximum transverse force, and a predetermined maximum torque. Such predetermined threshold values may be selectable for particular anatomies and/or dimensions of particular guide tubes, such as guide tubes (92, 192, 292, 392), for inhibiting overloading the anatomy during use. Alternatively, or in addition to the above monitoring of respective measured force component values for inhibiting overloading of the anatomy during use, the measured force component values may be selectable for particular guide tubes, such as guide tubes (92, 192, 292, 392), for inhibiting overloading of guide tubes during use or while cleaning. While such use may differ in some respects, it will be appreciated that monitoring via multi-directional sensor assembly (110) may be similarly performed. The invention is thus not intended to be unnecessarily limited to the use described herein.

Microprocessor (120) more particularly compares each respective force component value to the predetermined maximum longitudinal force, the predetermined maximum transverse force, and the predetermined maximum torque. In the event that all such force component values being monitored are below the predetermined threshold values, control system (116) simply continues monitoring the force component values in real-time. However, in the event that one or more force component values respectively meets or exceeds the predetermined maximum longitudinal force, the predetermined maximum transverse force, and the predetermined maximum torque, microprocessor (120) communicates a warning signal to controller (122). Controller (122) then directs feedback device (124) to generate an indication of the warning signal to the clinician. Feedback device (124) may include, but is not limited to, a visual feedback display configured to generate a visual indicia to the clinician, a tactile feedback generator configured to generate a tactile indicia to the clinician, and an audible feedback generator configured to generate an audible indicia to the clinician. Clinician may then actively respond by manipulating dilation instrument (20) to reduce the forced engagement between guide tube (92) and the anatomy. Once all the respective measured force component values return below predetermined threshold values, controller (122) directs feedback device (124) to terminate the indication of the warning signal to communicate that the guide tube (92) is again being operated in a desirable state.

While the above referenced multi-directional sensor assembly (110) is shown schematically in FIG. 2, FIGS. 3, 6, and 9 respectively illustrate a torque sensor assembly (210), a longitudinal force sensor assembly (310), and a transverse force sensor assembly (410). One or more of torque sensor assembly (210), longitudinal force sensor assembly (310), and transverse force sensor assembly (410) may be incorporated into dilation instrument assembly (10) to detect one or any combination of the longitudinal force, transverse force, and torque components similar to multi-directional sensor assembly (110). Various aspects of each of torque sensor assembly (210), longitudinal force sensor assembly (310), and transverse force sensor assembly (410) may be combined and/or exchanged in accordance with the invention described herein, and it will be appreciated that the invention is not intended to be unnecessarily limited to use with the exemplary sensor assemblies (110, 210, 310, 410) shown in FIGS. 2, 3, 6, and 9.

Moreover, multi-directional sensor assembly (110) is shown contained within port (94) of handle body (22) to indirectly engage with guide tube (92) via hub (90), whereas torque sensor assembly (210), longitudinal force sensor assembly (310), and transverse force sensor assembly (410) directly engage with other exemplary guide tubes (192, 292, 392). Accordingly, sensor assemblies (110, 210, 310, 410) may be directly or indirectly connected with guide tubes (92, 192, 292, 392) for operation, and the invention is not intended to be unnecessarily limited to either direct or indirect connections. As provided below, like numbers indicate like features discussed above.

A. Torque Sensor Assembly

Figure 3:
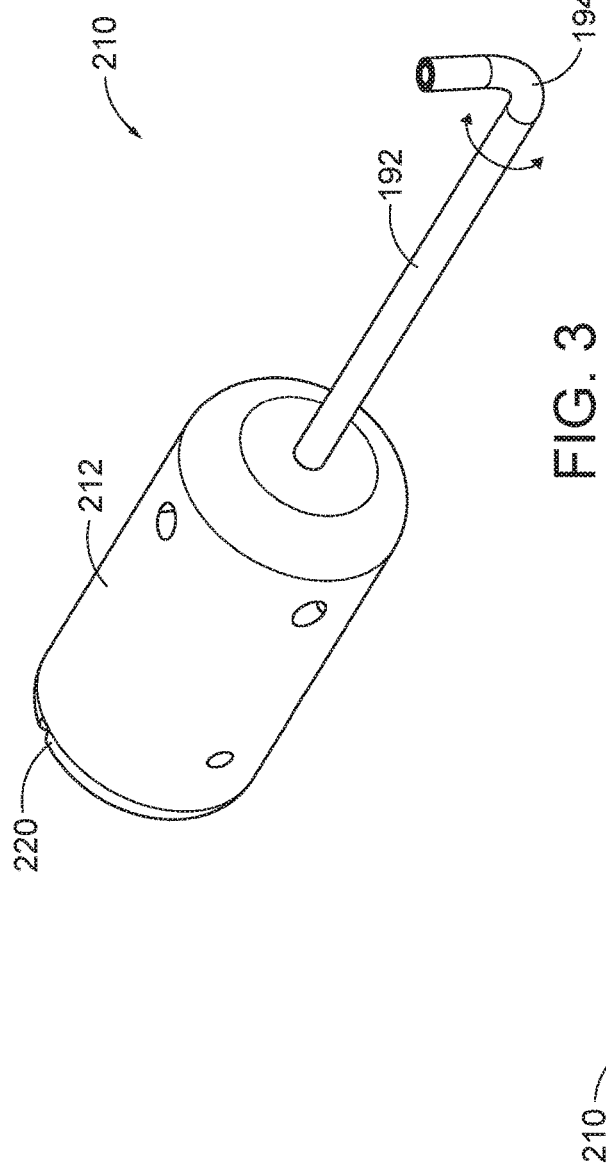
FIG. 3 depicts a perspective view of an exemplary torque sensor assembly for detecting a torque in the force measurement system of FIG. 2.
Figure 4:
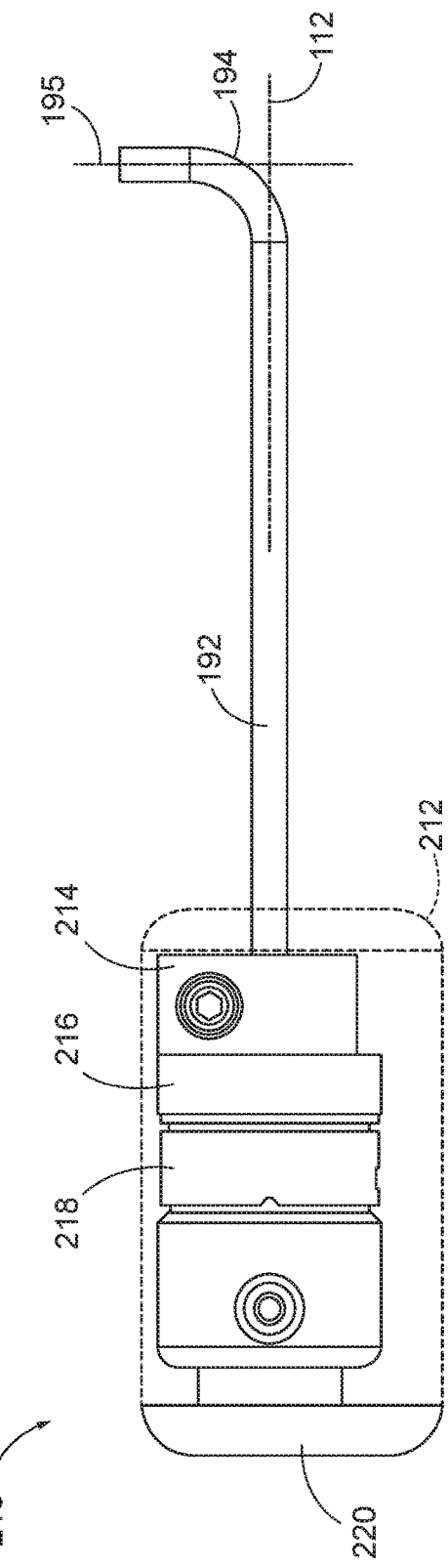
FIG. 4 depicts a side elevational view of the torque sensor assembly of FIG. 3 having various features hidden for clarity.
Figure 5:
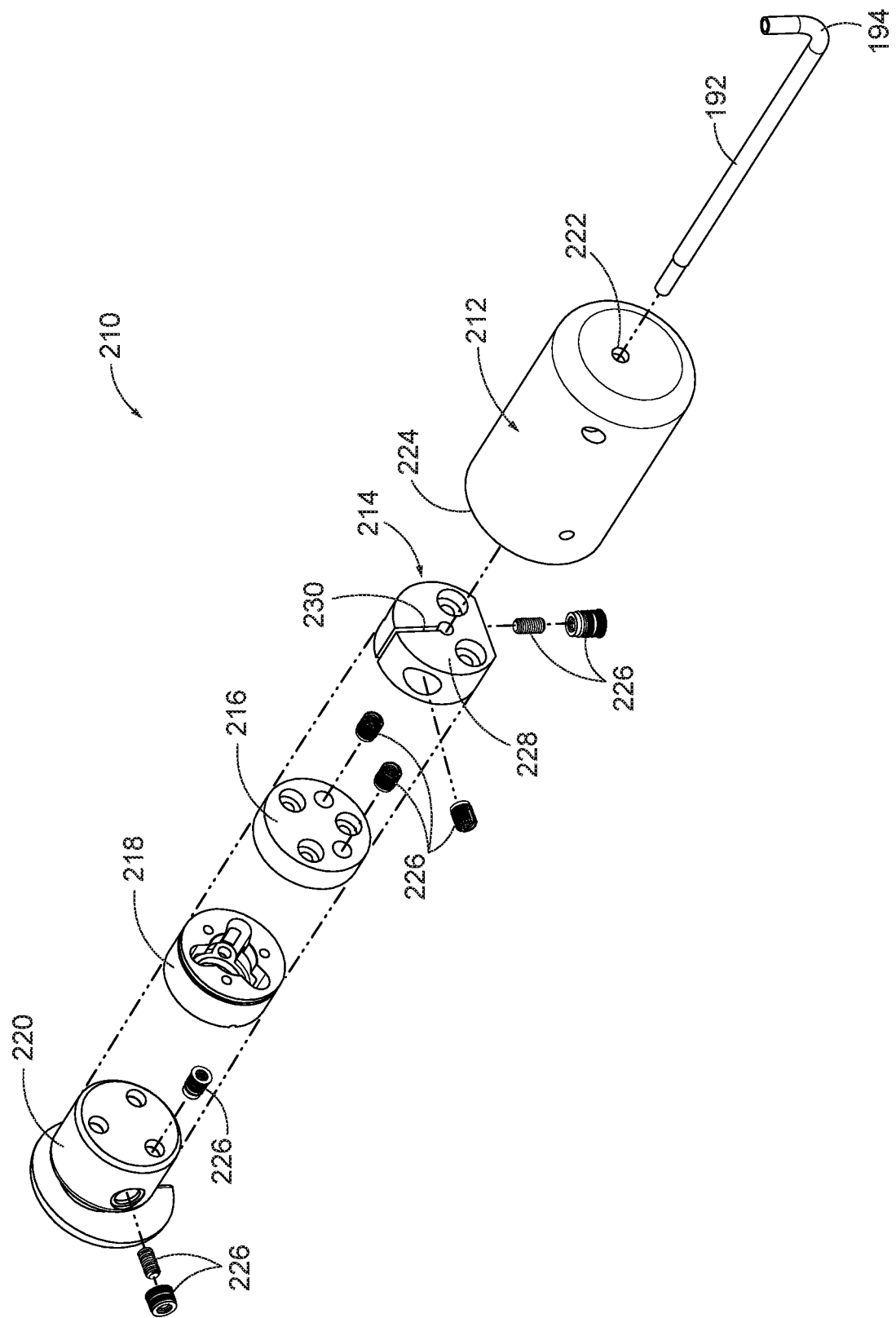
FIG. 5 depicts an exploded perspective view of the torque sensor assembly of FIG. 3.

FIGS. 3-5 show an exemplary torque sensor assembly (210) configured to detect torque applied to guide tube (192) for measurement by operative connection to the remainder of force measurement system (100) (see FIG. 2). In the present example, torque sensor assembly (210) replaces multi-directional sensor assembly (110) (see FIG. 2) for only detecting torque, but additional force component values may be detected and monitored as discussed above. Torque sensor assembly (210) thus operatively connects to data acquisition module (114) (see FIG. 2) and control system (116) (see FIG. 2) for measuring, storing, and/or monitoring force applied to guide tube (192) as discussed above with respect to multi-directional sensor assembly (110) (see FIG. 2).

In the present example, guide tube (192) has a preformed bend (194) bent approximately 90 degrees. Proximal end portion of guide tube (192) defines the longitudinal axis, whereas a distal end portion of guide tube (192) defines a distal axis (195) that is perpendicular to the longitudinal axis. Thus, guide tube (192) is configured to extend to anatomy that is perpendicular to an adjacent passageway for similarly guiding guidewire (30) (see FIG. 1A) and dilation catheter (40) (see FIG. 1A).

With respect to FIGS. 3 and 4, torque sensor assembly (210) generally includes a torque sensor housing (212), a torque guide tube mounting (214), a mounting adapter (216), a torque sensor (218), and a torque sensor base (220). Torque sensor housing (212) has a distal opening (222) configured to receive guide tube (192) and a proximal opening (224) configured to receive each of torque guide tube mounting (214), mounting adapter (216), and torque sensor (218) for containment within torque sensor housing (212). In addition, torque sensor base (220) is also received within proximal opening (224) to cover proximal opening (224) to secure torque guide tube mounting (214), mounting adapter (216), and torque sensor (218) within torque sensor housing (212). A plurality of fasteners (226) operatively secure torque sensor housing (212), torque guide tube mounting (214), mounting adapter (216), torque sensor (218), torque sensor base (220), and guide tube (192) relative to each other to isolate and transmit rotational movement of guide tube (192) to torque sensor (218) for use.

In the present example, FIG. 5 shows torque guide tube mounting (214) with a clamp (228) about a slotted opening (230), which is configured to receive guide tube (192). Clamp (228) compresses guide tube (192) to affix guide tube (192) relative to torque guide tube mounting (214). Thereby, guide tube mounting (214) is configured to rotate with guide tube (192) for transmitting rotation toward torque sensor (218). Mounting adapter (216) is secured directly between guide tube mounting (214) and torque sensor (218) to transmit rotation directly from guide tube mounting (214) and directly to torque sensor (218) for detection. Torque guide tube mounting (214), mounting adapter (216), torque sensor (218), and torque sensor base are thus longitudinally sandwiched together and radially captured within torque sensor housing (212) while allowing rotation to transfer to torque sensor (218) for detection.

A proximal portion of torque sensor (218) is secured directly to torque sensor base (220) to inhibit rotation of proximal portion of torque sensor (218) relative to torque sensor housing (212). A distal portion of torque sensor (218) is secured directly to mounting adapter (216) to transmit torque to the distal portion of torque sensor (218). A torque differential applied between the proximal and distal portions of torque sensors (218) generates an electrical response, such as a change in current, resistance, or voltage, in torque sensor (218) communicated to data acquisition module (114) (see FIG. 2) and control system (116). The specific electrical response is configured to indicate a particular measured torque, which is then monitored for use, such as those discussed herein.

In use, with respect to FIGS. 3-5, the clinician inserts guide tube (192) into the passageway through the anatomy of the patient. As clinician manipulates guide tube (192) guide tube (192) engages with the anatomy and, in the event that the engagement has a torque component, rotatably urges guide tube (192) about longitudinal axis (112) (see FIG. 2). Rotation of guide tube (192) similarly rotates torque guide tube mounting (214) and mounting adapter (216) to generate the torque differential between the distal and proximal portions of torque sensor (218) for detecting the torque.

B. Longitudinal Force Sensor Assembly

Figure 6:
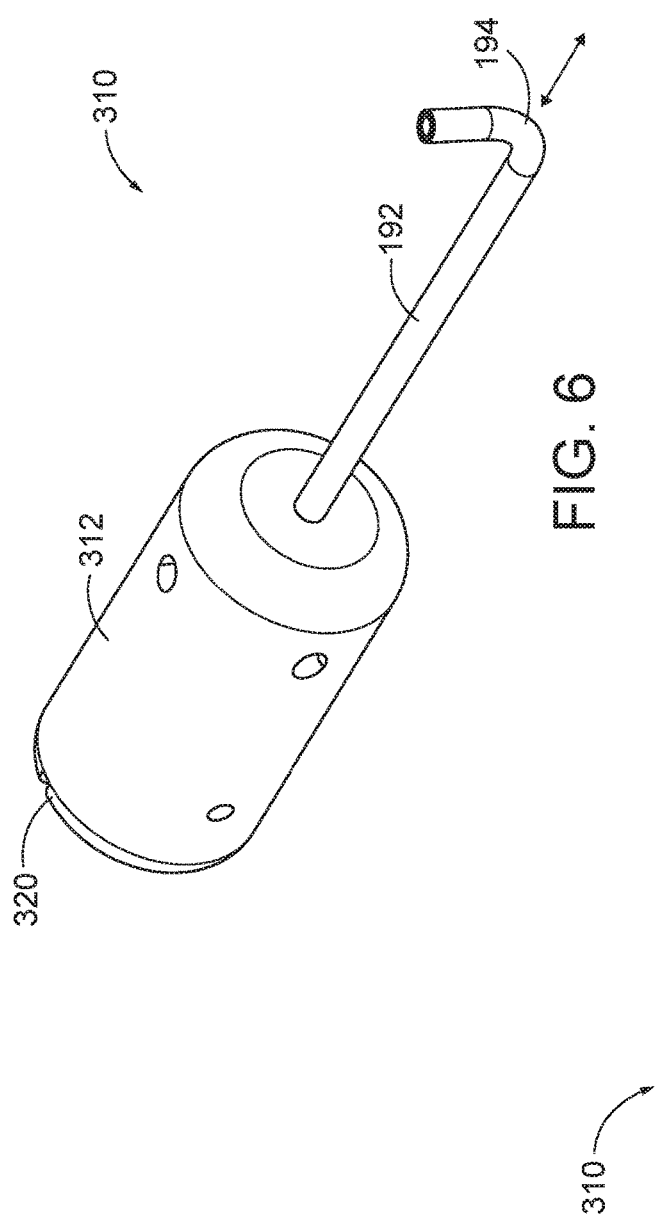
FIG. 6 depicts a perspective view of an exemplary longitudinal force sensor assembly for detecting a longitudinal force in the force measurement system of FIG. 2.
Figure 7:
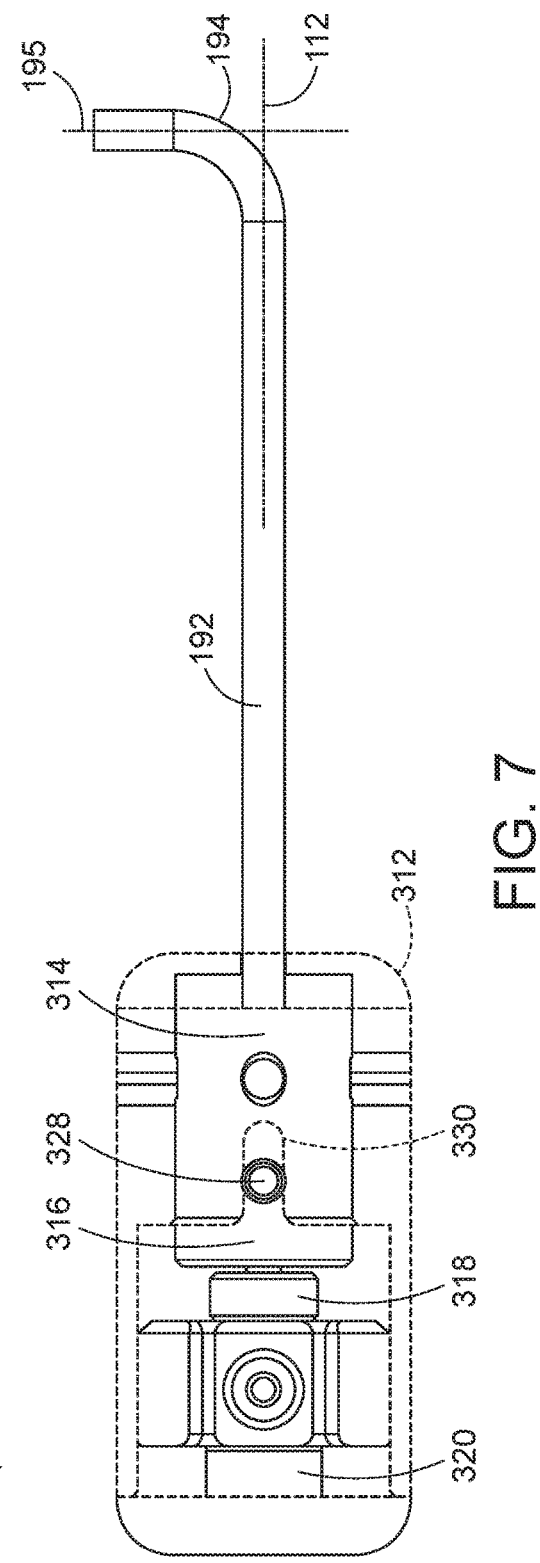
FIG. 7 depicts a side elevational view of the longitudinal force sensor assembly of FIG. 6 having various features hidden for clarity.
Figure 8:
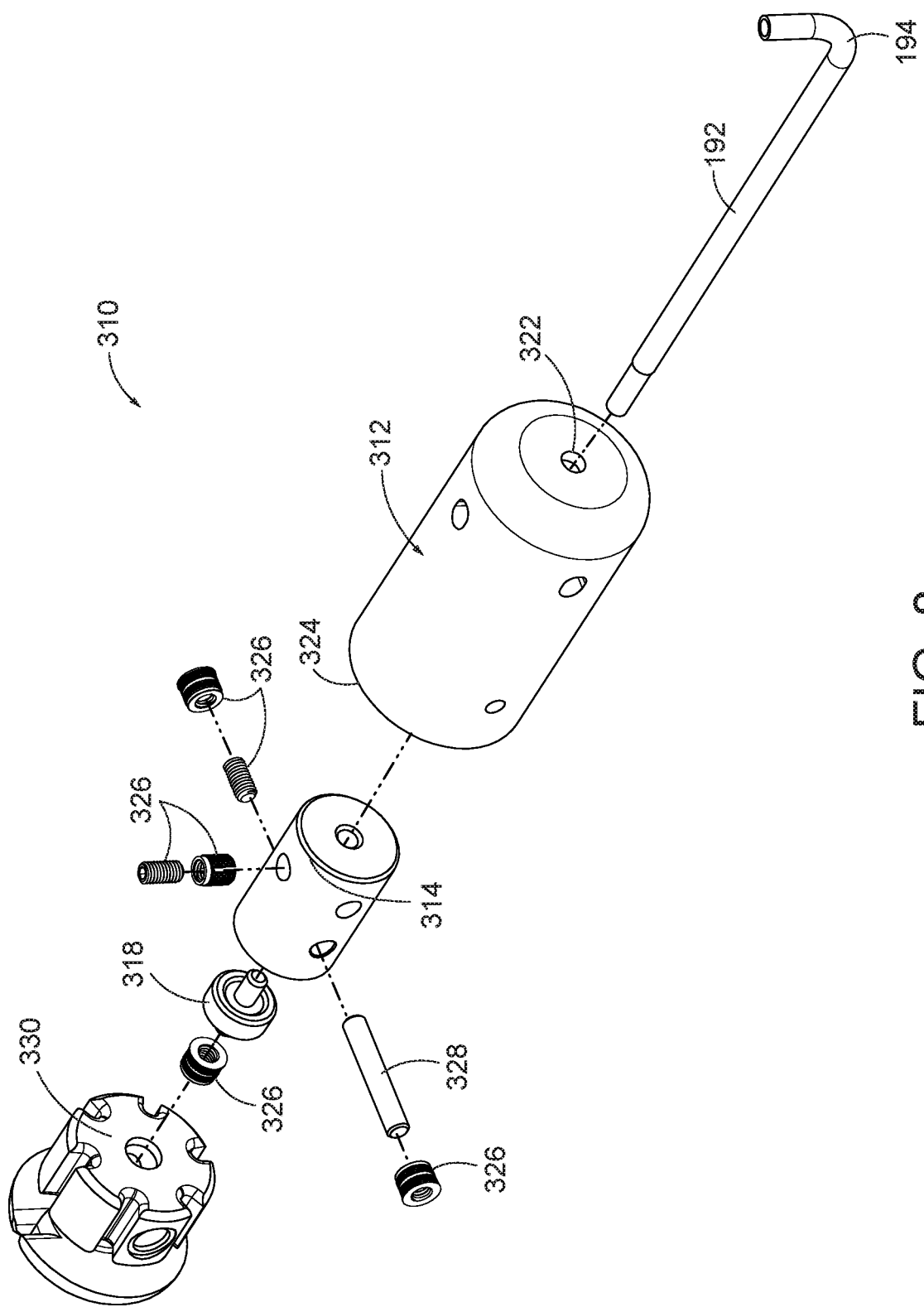
FIG. 8 depicts an exploded perspective view of the longitudinal force sensor assembly of FIG. 6.

FIGS. 6-8 show an exemplary longitudinal force sensor assembly (310) configured to detect longitudinal force applied to guide tube (192) for measurement by operative connection to the remainder of force measurement system (100) (see FIG. 2). In the present example, longitudinal force sensor assembly (310) replaces multi-directional sensor assembly (110) (see FIG. 2) for only detecting longitudinal force, but additional force component values may be detected and monitored as discussed above. Longitudinal force sensor assembly (310) thus operatively connects to data acquisition module (114) (see FIG. 2) and control system (116) (see FIG. 2) for measuring, storing, and/or monitoring force applied to guide tube (192) as discussed above with respect to multi-directional sensor assembly (110) (see FIG. 2).

With respect to FIGS. 6 and 7, longitudinal force sensor assembly (310) generally includes a longitudinal force sensor housing (312), a longitudinal force guide tube mounting (314), a longitudinal force adapter (316), a longitudinal force sensor (318), and a longitudinal force sensor base (320). Longitudinal force sensor housing (312) has a distal opening (322) configured to receive guide tube (192) and a proximal opening (324) configured to receive each of longitudinal force guide tube mounting (314), longitudinal force adapter (316), and longitudinal force sensor (318) for containment within longitudinal force sensor housing (312). In addition, longitudinal force sensor base (320) is also received within proximal opening (324) to cover proximal opening (324) to secure longitudinal force guide tube mounting (314), longitudinal force adapter (316), and longitudinal force sensor (318) within longitudinal force sensor housing (312). A plurality of fasteners (326) operatively secure longitudinal force sensor housing (312), longitudinal force guide tube mounting (314), longitudinal force adapter (316), longitudinal force sensor (318), longitudinal force sensor base (320), and guide tube (192) relative to each other to isolate and transmit axial, longitudinal movement of guide tube (192) to longitudinal force sensor (318) for use.

In the present example, FIGS. 7 and 8 show longitudinal force guide tube mounting (314) and longitudinal force adapter (316) formed together as a unitary structure. At least one of fasteners (326) thread into longitudinal force guide tube mounting (314) to compress guide tube (192) within a distal end portion of longitudinal force guide tube mounting (314). A proximal end portion of longitudinal force guide tube mounting (314) includes a pin (328) extending radially outward therefrom. Pin (328) is slidably received within a longitudinally extending slot (330) to inhibit rotation of longitudinal force guide tube mounting and adapter (314, 316), while longitudinal force guide tube mounting and adapter (314, 316) are also radially captured within longitudinal force sensor housing (312). A distal portion of longitudinal force sensor (318) is received against longitudinal force adapter (316) to detect longitudinal force thereagainst. Guide tube (192), longitudinal force guide tube mounting (314), and longitudinal force adapter (316) are secured together to be longitudinally urged relative to longitudinal force sensor (318) for detection against the distal portion of longitudinal force sensor (318).

A proximal portion of longitudinal force sensor (318) is secured directly to longitudinal force sensor base (320) to inhibit movement of the proximal portion of longitudinal force sensor (318) relative to longitudinal force sensor housing (312). A distal portion of longitudinal force sensor (318) received directly against longitudinal force adapter (316) transmits longitudinal force therealong to longitudinal force sensor (318). Compressing longitudinal force sensor (318) between the longitudinal force sensor base (320) and longitudinal force adapter (316) generates an electrical response, such as a change in current, resistance, or voltage, in longitudinal force sensor (318) communicated to data acquisition module (114) (see FIG. 2) and control system (116). The specific electrical response is configured to indicate a particular measured longitudinal force, which is then monitored for use, such as those discussed herein.

In use, with respect to FIGS. 6-8, the clinician inserts guide tube (192) into the passageway through the anatomy of the patient. As clinician manipulates guide tube (192), guide tube (192) engages with the anatomy and, in the event that the engagement has a longitudinal force component, longitudinally urges guide tube (192) in the proximal direction along longitudinal axis (112) (see FIG. 2). Proximally urging guide tube (192) similarly urges longitudinal force guide tube mounting (314) and longitudinal force adapter (316) to generate the compression of longitudinal force sensor (318) for detecting the longitudinal force.

C. Transverse Force Sensor Assembly

Figure 9:
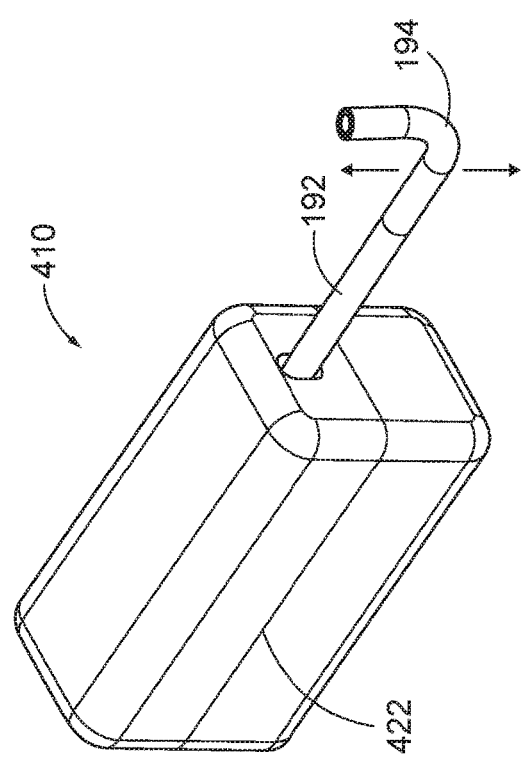
FIG. 9 depicts a perspective view of an exemplary transverse force sensor assembly for detecting a transverse force and a torque in the force measurement system of FIG. 2.
Figure 10:
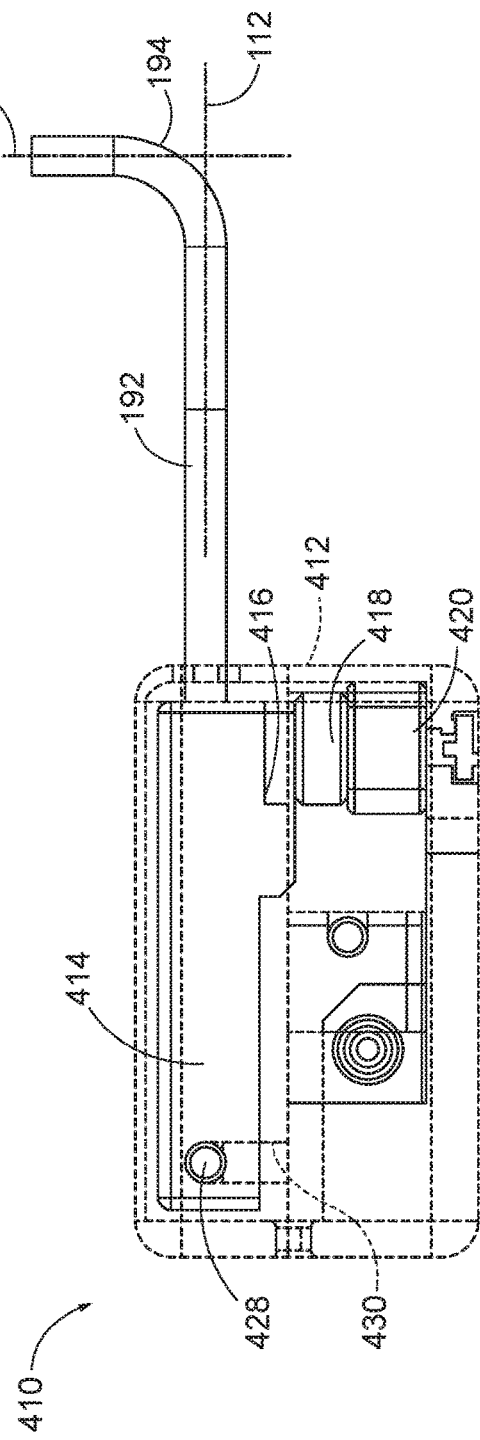
FIG. 10 depicts a side elevational view of the transverse force sensor assembly of FIG. 9 having various features hidden for clarity.
Figure 11:
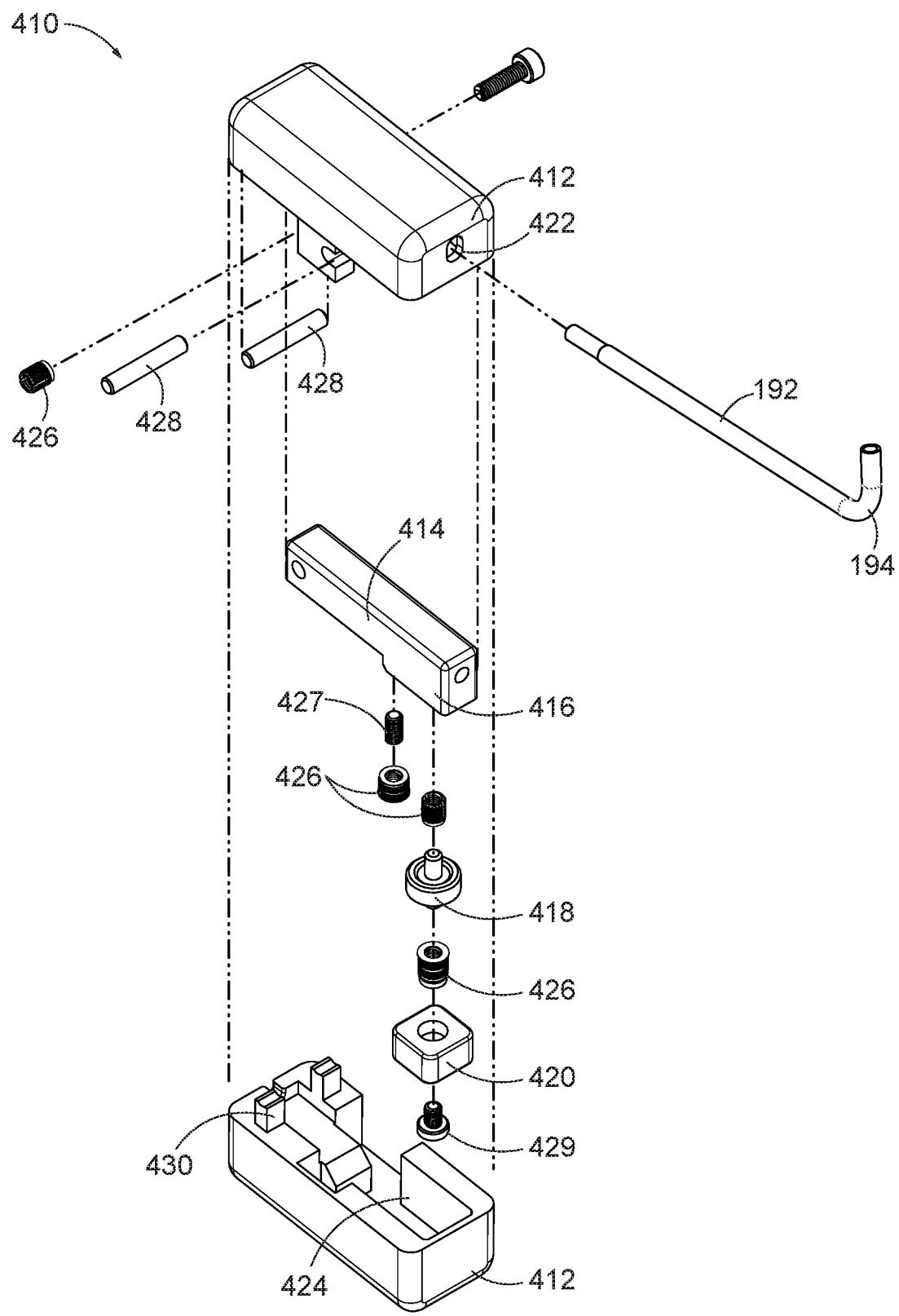
FIG. 11 depicts an exploded perspective view of the exemplary transverse force sensor assembly of FIG. 9.

FIGS. 9-11 show an exemplary transverse force sensor assembly (410) configured to detect transverse force and associated torque applied to guide tube (192) for measurement by operative connection to the remainder of force measurement system (100) (see FIG. 2). In the present example, transverse force sensor assembly (410) replaces multi-directional sensor assembly (110) (see FIG. 2) for only detecting transverse force, but additional force component values may be detected and monitored as discussed above. Transverse force sensor assembly (410) thus operatively connects to data acquisition module (114) (see FIG. 2) and control system (116) (see FIG. 2) for measuring, storing, and/or monitoring force applied to guide tube (192) as discussed above with respect to multi-directional sensor assembly (110) (see FIG. 2).

With respect to FIGS. 9 and 10, transverse force sensor assembly (410) generally includes a transverse force sensor housing (412), a transverse force guide tube mounting (414), a transverse force adapter (416), a transverse force sensor (418), and a transverse force sensor base (420). In the present example, transverse force guide tube mounting (414) and transverse force adapter (416) are formed together as a unitary structure. Transverse force sensor housing (412) has a distal opening (422) configured to receive guide tube (192) and an interior opening (424) configured to receive each of transverse force guide tube mounting (414), transverse force adapter (416), and transverse force sensor (418) for containment within transverse force sensor housing (412). A plurality of fasteners (426, 427, 429) operatively secure transverse force sensor housing (412), transverse force guide tube mounting (414), transverse force adapter (416), transverse force sensor (418), transverse force sensor base (420), and guide tube (192) relative to each other to isolate and transmit transverse movement of guide tube (192) to transverse force sensor (318) for use.

In the present example, FIGS. 10 and 11 show transverse force guide tube mounting (414) and transverse force adapter (416) at least partially formed together. A set screw (427) threads into transverse force guide tube mounting (414) to compress guide tube (192) within a distal end portion of transverse force guide tube mounting (414). A proximal end portion of transverse force guide tube mounting (314) is pivotally mounted about a pin (428). Pin (428) is received within a carrier (430) to inhibit rotation and axial movement of transverse force guide tube mounting and adapter (414, 416). An upper portion of transverse force sensor (418) is received against transverse force adapter (416) to detect transverse force thereagainst. A screw (429) operatively secures transverse force sensor (418) relative to transverse force adapter (416). Guide tube (192), transverse force guide tube mounting (414), and transverse force adapter (416) are secured together to be transversely urged relative to transverse force sensor (418) for detection against the upper portion of transverse force sensor (418).

A lower portion of transverse force sensor (418) is secured directly to transverse force sensor base (420) to inhibit movement of the lower portion of transverse force sensor (418) relative to transverse force sensor housing (412). An upper portion of transverse force sensor (418) received directly against transverse force adapter (416) transmits transverse force therealong to transverse force sensor (418). Compressing and/or decompressing transverse force sensor (418) between the transverse force sensor base (420) and transverse force adapter (416) generates an electrical response, such as a change in current, resistance, or voltage, in transverse force sensor (418) communicated to data acquisition module (114) (see FIG. 2) and control system (116). The specific electrical response is configured to indicate a particular measured transverse force, which is then monitored for use, such as those discussed herein.

In use, with respect to FIGS. 9-11, the clinician inserts guide tube (192) into the passageway through the anatomy of the patient. As clinician manipulates guide tube (192) guide tube (192) engages with the anatomy and, in the event that the engagement has a transverse force component, transversely urges guide tube (192) in the upper or lower direction transverse to the longitudinal axis (112) (see FIG. 2). Transversely urging guide tube (192) similarly urges transverse force guide tube mounting (414) and transverse force adapter (416) to generate the compression or decompression of transverse force sensor (418) for detecting the transverse force.

D. Alternative Guide Catheters

Figure 12:
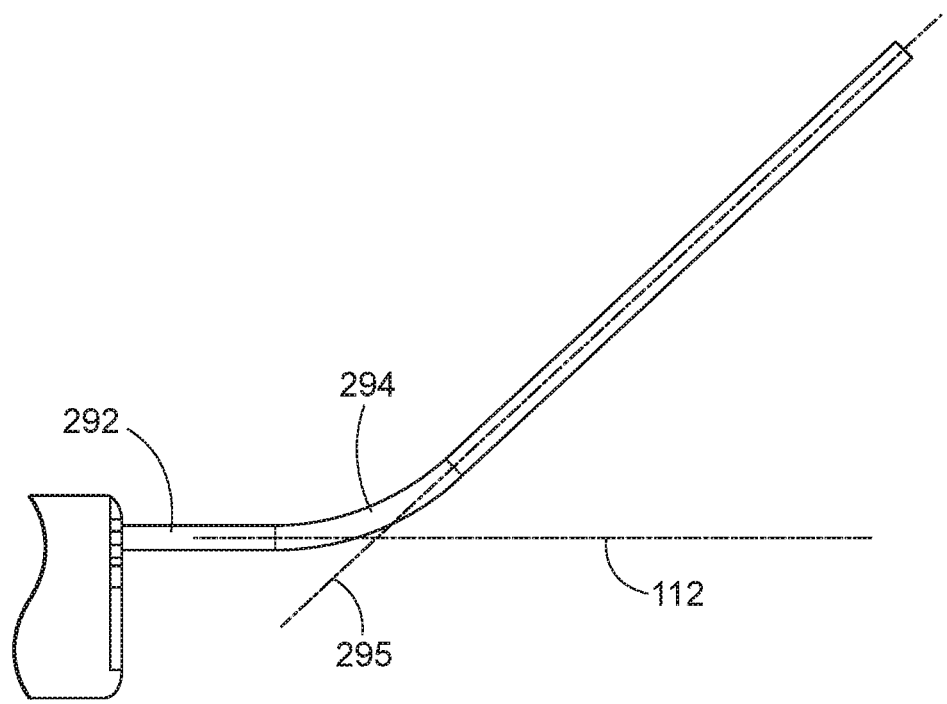
FIG. 12 depicts a side elevational view of an alternative guide tube.
Figure 13:
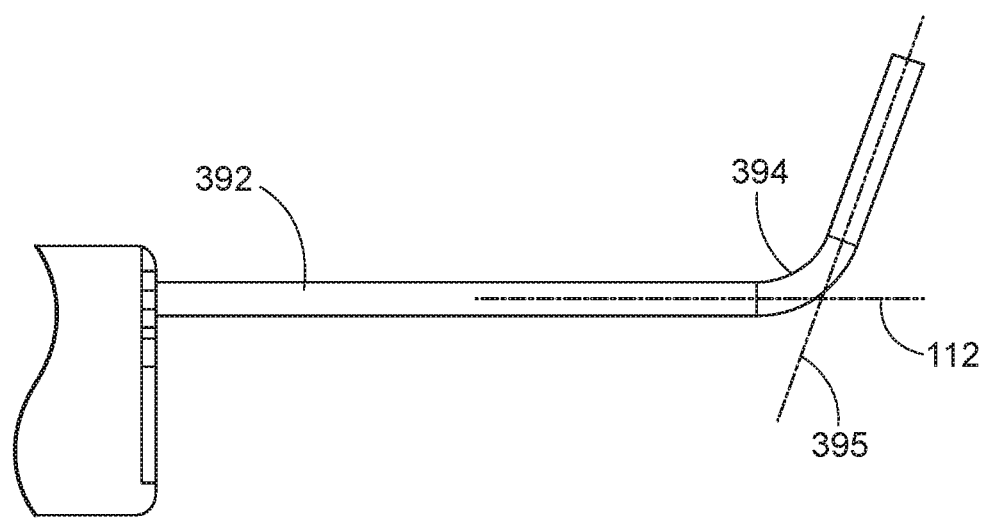
FIG. 13 depicts a side elevational view of another alternative guide tube.

FIGS. 12 and 13 show alternative guide tubes (292, 392) having respective preformed bends (294, 394). Preformed bend (294) is bent to approximately 135 degrees, and preformed bend (394) is bent to approximately 110 degrees. Proximal end portions of guide tubes (292, 392) each respectively define longitudinal axis (112), whereas distal end portions of guide tubes (292, 392) each define distal axes (295, 395) that are respectively approximately 135 degrees and 110 degrees to longitudinal axis (112). Thus, guide tubes (292, 392) are configured to extend to anatomy that is offset from an adjacent passageway approximately 135 degrees and 110 degrees for similarly guiding guidewire

Figure 1B:
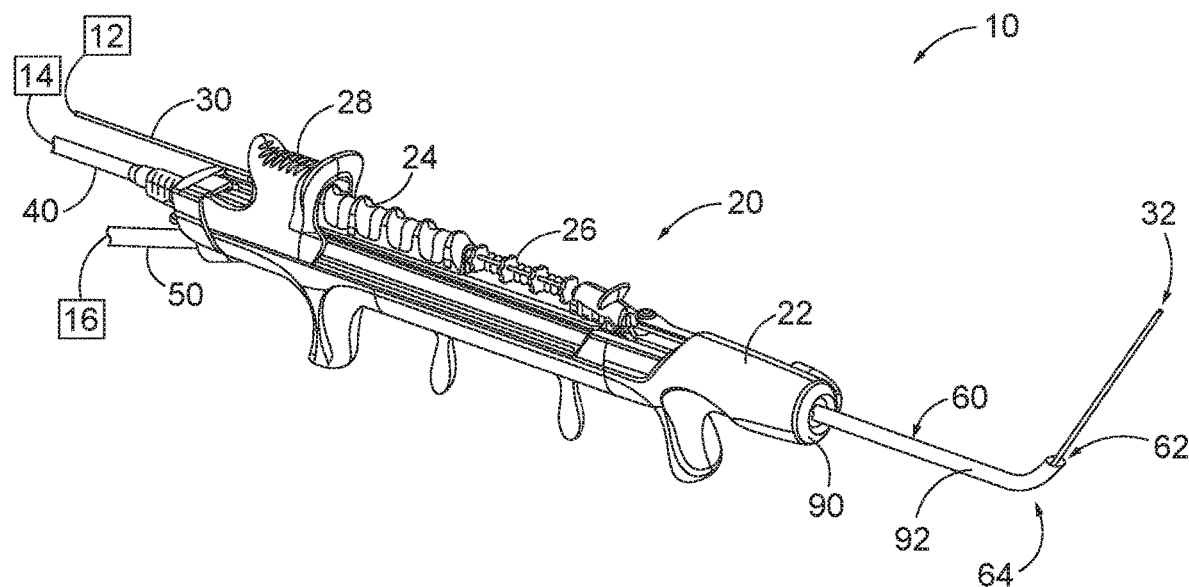
FIG. 1B depicts a perspective view of the dilation instrument assembly of FIG. 1A, with the guidewire in a distal position, and with the dilation catheter in the proximal position.
Figure 1C:
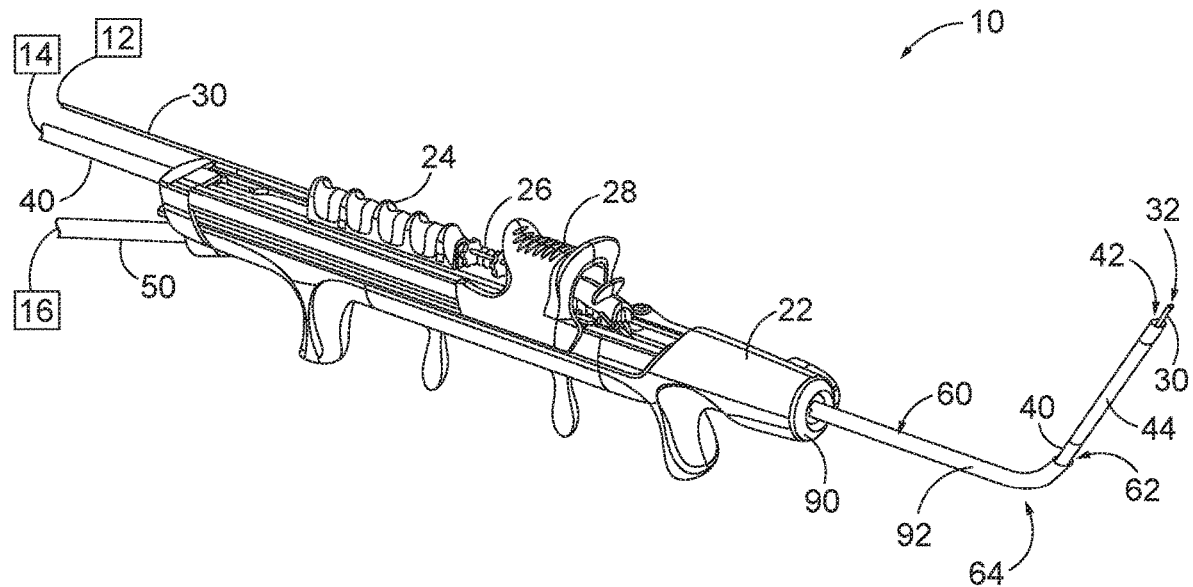
FIG. 1C depicts a perspective view of the dilation instrument assembly of FIG. 1A, with the guidewire in a distal position, with the dilation catheter in a distal position, and with a dilator of the dilation catheter in a non-dilated state.
Figure 1D:
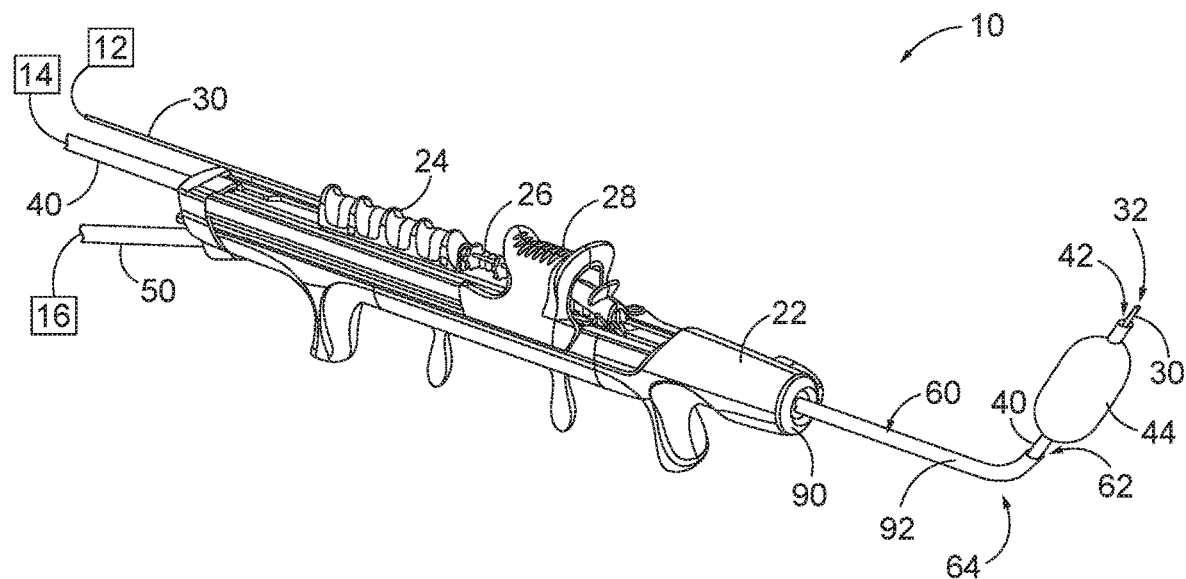
FIG. 1D depicts a perspective view of the dilation instrument assembly of FIG. 1A, with the guidewire in a distal position, with the dilation catheter in the distal position, and with a dilator of the dilation catheter in a dilated state.

(30) (see FIG. 1A) and dilation catheter (40) (see FIG. 1A). It will be appreciated that alternative angles for accessing one or more anatomies may be similarly used, and the invention is not intended to be unnecessarily limited to particular guide tubes shown and described herein.

E. Guide Tube with Integral Force Sensor

Figure 14:
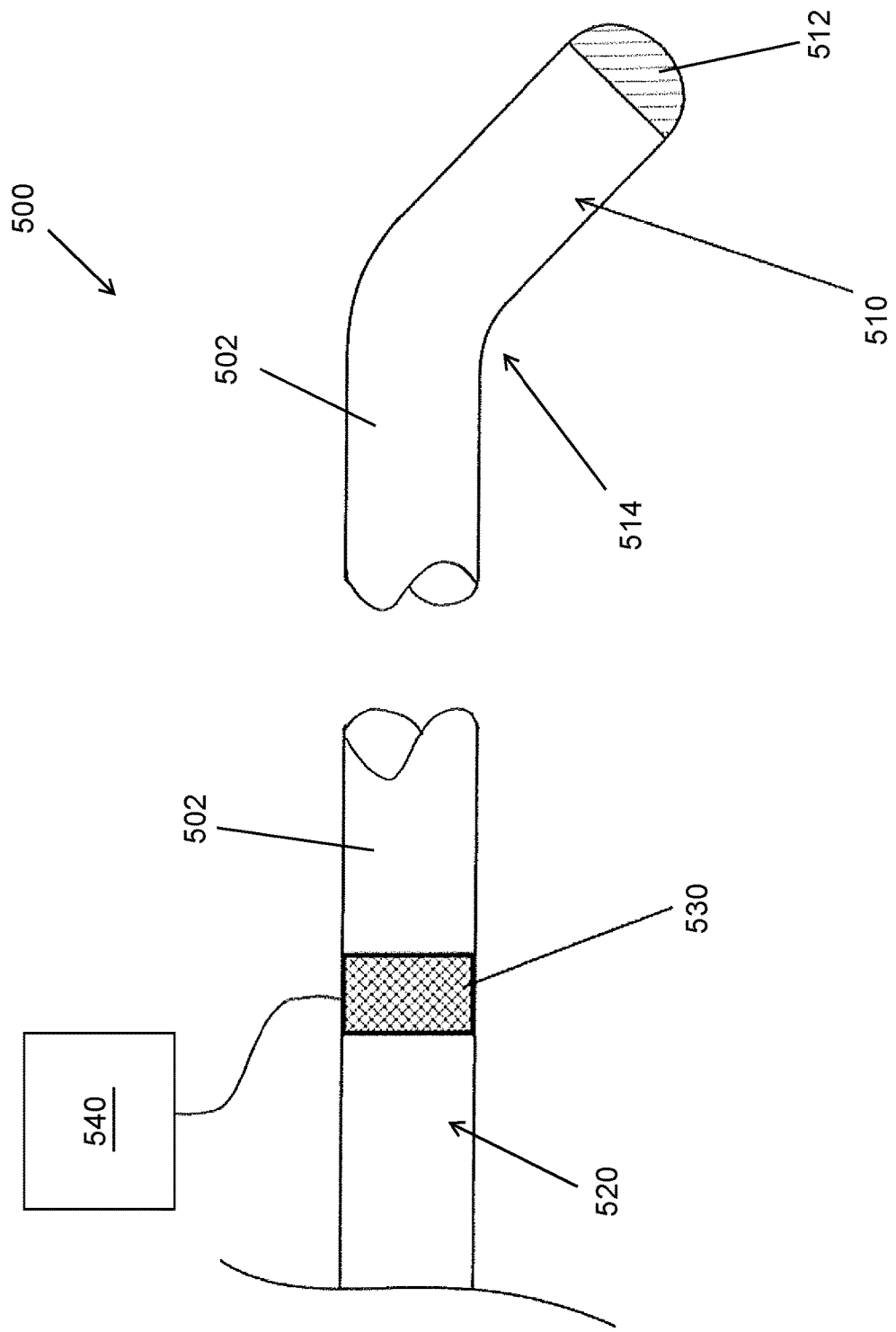
FIG. 14 depicts a schematic view of another alternative guide tube with an integral force sensor.

While the examples described above with reference to FIGS. 2-11 include various sensor assemblies (110, 210, 310, 410) that are coupled with a proximal end of a guide tube (92, 192, 292, 392), it may be desirable to provide a guide tube that has a force sensor directly integrated onto the shaft of the guide tube. This may provide a reduced form factor and otherwise simplify the design of an instrument incorporating such a force sensor. FIG. 14 shows an example of a guide tube (500) with an integral force sensor (530). As with guide tubes (192, 292, 392) described above, guide tube (500) of this example may be readily incorporated into dilation instrument (20) in place of guide tube (92).

While force sensor (530) is described below as being integrated with guide tube (500), force sensor (530) may alternatively be integrated with various other kinds of structures. By way of example only, force sensor (530) may instead be integrated with a guide rail along which an externally positioned dilation catheter (40) translates. As another merely illustrative example, force sensor (530) may be integrated into a dilation catheter (40), an ablation catheter, a pointer, a probe, a tissue shaver, some other kind of investigative instrument. Other structures in which force sensor (530) may be integrated will be apparent to those skilled in the art in view of the teachings herein.

Guide tube (500) of the present example comprises a shaft body (502), a distal portion (510), and a proximal portion (520). Distal portion (510) includes a distal tip (512) and a preformed bend (514) that is proximal to distal tip (512). In the present example, shaft body (502) is substantially rigid, such that forces (e.g., torque, longitudinal force, transverse force, etc.) imparted at distal portion (510) will be communicated along the length of shaft body (502) to proximal portion (520). By way of example only, shaft body (502) may be formed of a metal (e.g., stainless steel, etc.), a plastic (e.g., PEEK, etc.), and/or any other suitable material(s) as will be apparent to those skilled in the art in view of the teachings herein.

Force sensor (530) is coaxially positioned about the proximal portion (520) of shaft body (502). Force sensor (530) is operable to detect forces exerted on the proximal portion (520) of shaft body (502), as communicated along the length of shaft body (502), in response to forces imparted at distal portion (510) of shaft body (502). By way of example only, force sensor (530) may be in the form of a flex circuit or other thin film assembly that is wrapped about the proximal portion (520) of shaft body (502) and secured to shaft body (502) using an adhesive and/or using other techniques. Force sensor (530) may thus provide a relatively low profile that does not require substantial spatial accommodations around the proximal portion (520) of shaft body (502). By way of further example only, force sensor (530) may comprise one or more strain gauges. Other suitable forms that force sensor (530) may take will be apparent to those skilled in the art in view of the teachings herein.

Force sensor (530) may be configured to sense torque, longitudinal force, and/or transverse force, at the proximal portion (520) of shaft body (502). This sensed force may correlate with the same force being imparted at distal portion (510) of shaft body (502). In some instances, the sensed force may be substantially less at proximal portion (520) than the force at distal portion (510), but the reduction in force as communicated along the length of shaft body (502) may be known, such that it is possible to calculate the force at distal portion (510) based on the force sensed at proximal portion (520). Various suitable ways in which such a calculation may be carried out will be apparent to those skilled in the art in view of the teachings herein.

Force sensor (530) is coupled with a data acquisition module (540). By way of example only, force sensor (530) may be coupled with data acquisition module (540) via wires, conductive traces, inductive coupling, or otherwise. Data acquisition module (540) may be configured and operable just like data acquisition module (114) described above. Moreover, data acquisition module (540) may be further coupled with, or integrated into, control system (116) as described above. Control system (116) may thus monitor force data from force sensor (530) and provide alerts to the operator and/or other reactions when the force data from force sensor (530) exceeds a threshold value. Thus, force sensor (530) and control system (116) may cooperate to ensure that the operator does not damage an anatomical structure (e.g., the patient's brain, optic nerve, etc.) with distal portion (510) of guide tube (500).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation instrument, comprising: (a) a body; (b) a guidewire operatively connected to the body and configured to move relative to the body; (c) a dilation catheter having an expandable dilator operatively connected to the body and configured to move relative to the body, wherein the dilation catheter is configured to movably receive the guidewire therein for guiding movement of the expandable dilator along the guidewire; (d) a guide member extending distally from the body along a longitudinal axis, wherein the guidewire and the dilation catheter are configured to translate relative to the guide member, wherein the guide member is configured to guide the guidewire and the dilation catheter as the guidewire and the guidewire translate relative to the guide member; and (e) a force measurement system operatively connected to the guide member and configured to measure a force received against the guide member for monitoring engagement with an anatomy of a patient.

Example 2

The dilation instrument of Example 1, wherein the force measurement system is configured to measure a longitudinal force component of the force, and wherein the longitudinal force component is axially along the longitudinal axis.

Example 3

The dilation instrument of Example 2, wherein the force measurement system further includes a guide mounting configured to limit movement of the guide member to a longitudinal direction relative to the longitudinal axis.

Example 4

The dilation instrument of any one or more of Examples 1 through 3, wherein the force measurement system is configured to measure a transverse force component of the force, and wherein the transverse force component is transverse to the longitudinal axis.

Example 5

The dilation instrument of Example 4, wherein the force measurement system further includes a guide mounting configured to limit movement of the guide member to a transverse direction relative to the longitudinal axis.

Example 6

The dilation instrument of any one or more of Examples 1 through 5, wherein the force measurement system is configured to measure a torque associated with the force, and wherein the torque is a moment about the longitudinal axis.

Example 7

The dilation instrument of Example 6, wherein the force measurement system further includes a guide mounting configured to limit movement of the guide member to a rotational direction about the longitudinal axis.

Example 8

The dilation instrument of any one or more of Examples 1 through 7, wherein the force measurement system is configured to measure a longitudinal component of the force, a transverse force component of the force, and a torque associated with the force, wherein the longitudinal force component is axially along the longitudinal axis, wherein the transverse force component is transverse to the longitudinal axis, and wherein the torque is a moment about the longitudinal axis.

Example 9

The dilation instrument of any one or more of Examples 1 through 8, wherein the guide member further includes a guide tube having a proximal tubular portion and a distal tubular portion, wherein the proximal tubular portion defines the longitudinal axis, wherein the force measurement system further includes a sensor operatively connected to the guide tube and configured to detect the force for measurement.

Example 10

The dilation instrument of any one or more of Examples 1 through 9, wherein the force measurement system further includes: (i) a sensor operatively connected to the guide member to detect the force received against the guide member, and (ii) a control system operatively connected to the sensor and configured to measure the force detected by the sensor.

Example 11

The dilation instrument of Example 10, wherein the control system further includes a feedback device configured to indicate the measured force to the user.

Example 12

The dilation instrument of Example 11, wherein the control system further includes a controller operatively connected to the feedback device and the sensor, and wherein the controller is configured to direct the feedback device to indicate that the measured force is at least a predetermined threshold force for inhibiting overloading of the guide member during use.

Example 13

The dilation instrument of Example 12, wherein the feedback device is selected from the group consisting of: a visual feedback display and a tactile feedback generator.

Example 14

The dilation instrument of any one or more of Examples 10 through 13, wherein the force measurement system further includes a data acquisition system operatively connected to the sensor and configured to collect a detected force data from the sensor.

Example 15

The dilation instrument of any one or more of Examples 1 through 14, wherein the guide member comprises a guide catheter, wherein the dilation catheter is slidably disposed within the guide catheter.

Example 16

A dilation instrument, comprising: (a) a guide member, including: (i) a hub configured to releasably connect within a port of a body, and (ii) a guide tube distally extending from the hub and defining a longitudinal axis, wherein the guide tube is configured to guide a dilation catheter along a sinus passageway within a patient; and (b) a force measurement system including a sensor configured to operatively connect to the guide tube, wherein the sensor is configured to detect a force received against the guide tube for monitoring engagement with an anatomy along the passageway within the patient.

Example 17

The dilation instrument of Example 16, wherein the force measurement system is configured to measure at least one of a longitudinal component of the force, a transverse force component of the force, and a torque associated with the force, wherein the longitudinal force component is axially along the longitudinal axis, wherein the transverse force component is transverse to the longitudinal axis, and wherein the torque is a moment about the longitudinal axis.

Example 18

A method of dilating an ostium within a patient, comprising: (a) inserting a guide member within a passageway through an anatomy toward the ostium within the patient; (b) engaging the guide member against the anatomy; (c) measuring a force applied to the guide member via a force measurement system when the guide member is engaged with the anatomy; (d) guiding a dilation catheter along the guide member adjacent to the ostium; and (e) dilating the ostium with the dilation catheter.

Example 19

The method of Example 18, wherein the guide member defines a longitudinal axis and measuring the force further includes measuring at least one of a longitudinal component of the force, a transverse force component of the force, and a torque associated with the force, wherein the longitudinal force component is axially along the longitudinal axis, wherein the transverse force component is transverse to the longitudinal axis, and wherein the torque is a moment about the longitudinal axis.

Example 20

The method of any one or more of Examples 18 through 19, further comprising providing feedback of the measured force applied to the guide member to a user.

Example 21

A dilation instrument, comprising: (a) a body; (b) a dilation catheter having an expandable dilator, the dilation catheter being configured to move relative to the body; (d) a guide member extending distally from the body, wherein the dilation catheter is configured to translate relative to the guide member, wherein the guide member is configured to guide the dilation catheter as the dilation catheter translates relative to the guide member; and (e) a force sensor operatively connected to the guide member and configured to sense a force imparted against a distal end of the guide member for monitoring engagement with an anatomy of a patient.

Example 22

The dilation instrument of Example 21, wherein the force sensor is configured to measure a longitudinal force component of force oriented along a longitudinal axis of the guide member.

Example 23

The dilation instrument of any one or more of Examples 21 through 22, wherein the force sensor is positioned at a proximal portion of the guide member.

Example 24

The dilation instrument of any one or more of Examples 21 through 23, wherein the force sensor is configured to measure a transverse force component of the force oriented along a path that is transverse to a longitudinal axis of the guide member.

Example 25

The dilation instrument of any one or more of Examples 21 through 24, wherein the force sensor is coaxially positioned relative to the guide member.

Example 26

The dilation instrument of any one or more of Examples 21 through 25, wherein the force sensor is configured to measure a torque associated with the force oriented along a path that is angular about a longitudinal axis of the guide member.

Example 27

The dilation instrument of any one or more of Examples 21 through 26, wherein the force sensor comprises a strain gauge.

Example 28

The dilation instrument of any one or more of Examples 21 through 27, wherein the force sensor comprises a flex circuit wrapped about a proximal portion of the guide member.

Example 29

The dilation instrument of any one or more of Examples 21 through 28, wherein the guide member comprises a guide tube.

Example 30

The dilation instrument of any one or more of Examples 21 through 29, wherein the guide member is rigid.

Example 31

The dilation instrument of any one or more of Examples 21 through 30, wherein the guide member has a proximal portion defining a first longitudinal axis and a distal portion defining a second longitudinal axis, wherein the second longitudinal axis is oriented obliquely relative to the first longitudinal axis.

Example 32

The dilation instrument of Example 31, wherein the guide member further includes a preformed bend between the proximal portion and the distal portion.

Example 33

The dilation instrument of Example 32, wherein the preformed bend is rigid.

Example 34

The dilation instrument of any one or more of Examples 21 through 33, further comprising: (a) a processing module in communication with the force sensor; and (b) a feedback device in communication with the processing module, wherein the processing module is configured to drive the feedback device to provide feedback to an operator in response to the force exceeding a threshold.

Example 35

The dilation instrument of Example 34, wherein the feedback device is operable to provide one or more of audible feedback or tactile feedback.

Example 36

The dilation instrument of any one or more of Examples 21 through 35, wherein the dilation catheter is slidably disposed within an interior of the guide member.

Example 37

A dilation instrument, comprising: (a) a body; (b) a dilation catheter having an expandable dilator, the dilation catheter being configured to move relative to the body; (d) a guide member extending distally from the body, the guide member having a rigid shaft body with a bent distal portion, wherein the dilation catheter is configured to translate relative to the guide member, wherein the guide member is configured to guide the dilation catheter as the dilation catheter translates relative to the guide member; and (e) a force sensor unitarily coupled to the guide member, the force sensor being positioned at a proximal portion of the guide member, the force sensor being configured to sense a force imparted against the bent distal portion of the guide member.

Example 38

The dilation instrument of Example 37, wherein the proximal portion of the guide member is cylindraceous and has an exterior, wherein the force sensor is wrapped coaxially about the exterior of the proximal portion of the guide member.

Example 39

A method of addressing an anatomical passageway within a head of a patient, the method comprising: (a) inserting a guide member into a head of a patient and toward the anatomical passageway within the head of the patient; (b) engaging a distal portion of the guide member against an anatomical structure within the head of the patient such that the anatomical structure imparts a force against the guide member; (c) measuring the force imparted to the distal portion of guide member by the anatomical structure, wherein the force is measured using a force sensor, wherein the force sensor is secured to a proximal portion of the guide member; and (d) receiving an alert from a feedback device if the measured force exceeds a threshold, wherein the feedback device is driven based on signals from the force sensor.

Example 40

The method of Example 39, further comprising: (a) guiding a dilation catheter along the guide member to thereby position a dilator of the dilation catheter in the anatomical passageway; and (b) expanding the dilator to thereby dilate the anatomical passageway.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and, if necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation instrument, comprising:
   (a) a body;
   (b) a dilation catheter having an expandable dilator, the dilation catheter being configured to move relative to the body;
   (c) a guide member extending distally from the body, wherein the dilation catheter is configured to translate relative to the guide member, wherein the guide member is configured to guide the dilation catheter as the dilation catheter translates relative to the guide member; and
   (d) a force sensor operatively connected to the guide member and configured to sense a force imparted against a distal end of the guide member for monitoring engagement with an anatomy of a patient,
   wherein the guide member has a proximal portion defining a first longitudinal axis and a distal portion defining a second longitudinal axis, wherein the second longitudinal axis is oriented obliquely relative to the first longitudinal axis, wherein the guide member further includes a preformed bend between the proximal portion and the distal portion, wherein the preformed bend is rigid.

2. The dilation instrument of claim 1, wherein the force sensor is configured to measure a longitudinal force component of force oriented along a longitudinal axis of the guide member.

3. The dilation instrument of claim 1, wherein the force sensor is positioned at a proximal portion of the guide member.

4. The dilation instrument of claim 1, wherein the force sensor is configured to measure a transverse force component of the force oriented along a path that is transverse to a longitudinal axis of the guide member.

5. The dilation instrument of claim 1, wherein the force sensor is coaxially positioned relative to the guide member.

6. The dilation instrument of claim 1, wherein the force sensor is configured to measure a torque associated with the force oriented along a path that is angular about a longitudinal axis of the guide member.

7. The dilation instrument of claim 1, wherein the force sensor comprises a strain gauge.

8. The dilation instrument of claim 1, wherein the force sensor comprises a flex circuit wrapped about a proximal portion of the guide member.

9. The dilation instrument of claim 1, wherein the guide member comprises a guide tube.

10. The dilation instrument of claim 1, wherein the guide member is rigid.

11. The dilation instrument of claim 1, further comprising:
    (a) a processing module in communication with the force sensor; and
    (b) a feedback device in communication with the processing module, wherein the processing module is configured to drive the feedback device to provide feedback to an operator in response to the force exceeding a threshold.

12. The dilation instrument of claim 11, wherein the feedback device is operable to provide one or more of audible feedback or tactile feedback.

13. The dilation instrument of claim 1, wherein the dilation catheter is slidably disposed within an interior of the guide member.

14. The dilation instrument of claim 1, wherein the distal end of the guide member is rigid.

15. A dilation instrument, comprising:
    (a) a body;
    (b) a dilation catheter having an expandable dilator, the dilation catheter being configured to move relative to the body;
    (c) a guide member extending distally from the body, the guide member having a rigid shaft body with a bent distal portion, wherein the dilation catheter is configured to translate relative to the guide member, wherein the guide member is configured to guide the dilation catheter as the dilation catheter translates relative to the guide member; and
    (d) a force sensor unitarily coupled to the guide member, the force sensor being positioned at a proximal portion of the guide member, the force sensor being configured to sense a force imparted against the bent distal portion of the guide member.

16. The dilation instrument of claim 15, wherein the proximal portion of the guide member is cylindraceous and has an exterior, wherein the force sensor is wrapped coaxially about the exterior of the proximal portion of the guide member.

17. The dilation instrument of claim 15, wherein the guide member terminates in a rigid distal end.

18. A method of addressing an anatomical passageway within a head of a patient, the method comprising:
    (a) inserting a guide member into a head of a patient and toward the anatomical passageway within the head of the patient;
    (b) engaging a distal portion of the guide member against an anatomical structure within the head of the patient such that the anatomical structure imparts a force against the guide member;
    (c) measuring the force imparted to the distal portion of the guide member by the anatomical structure, wherein the force is measured using a force sensor, wherein the force sensor is secured to a proximal portion of the guide member;
    (d) receiving an alert from a feedback device if the measured force exceeds a threshold, wherein the feedback device is driven based on signals from the force sensor; and
    (e) guiding a dilation catheter through the guide member to thereby position a dilator of the dilation catheter in the anatomical passageway.

19. The method of claim 18, further comprising expanding the dilator to thereby dilate the anatomical passageway.

20. The method of claim 18, wherein guiding the dilation catheter through the guide member includes advancing the dilation catheter along a guidewire.

* * * * *